United States Patent [19]

McLane et al.

[11] Patent Number: 5,021,451

[45] Date of Patent: Jun. 4, 1991

[54] METHOD FOR INHIBITING HYPERPROLIFERATIVE DISEASES

[75] Inventors: John A. McLane, West Haven, Conn.; Milan R. Uskokovic, Upper Montclair, N.J.

[73] Assignee: Hoffman-La Roche Inc., Nutley, N.J.

[21] Appl. No.: 270,983

[22] Filed: Nov. 14, 1988

[51] Int. Cl.$^5$ ............................................. B61K 31/35
[52] U.S. Cl. ..................... 514/460; 514/863
[58] Field of Search ................................ 514/460, 263

[56] References Cited

U.S. PATENT DOCUMENTS

| | | | |
|---|---|---|---|
| 4,231,938 | 11/1980 | Monaghan et al. | 260/343.5 |
| 4,293,496 | 10/1981 | Willard | 260/343.5 |
| 4,294,926 | 10/1981 | Monaghan et al. | 424/125 |
| 4,346,227 | 8/1982 | Terahara et al. | 560/119 |
| 4,444,784 | 4/1984 | Hoffman et al. | 424/279 |
| 4,450,171 | 5/1984 | Hoffman et al. | 424/279 |
| 4,582,915 | 4/1986 | Sleteinger et al. | 549/292 |
| 4,668,699 | 5/1987 | Hoffman et al. | 514/460 |

FOREIGN PATENT DOCUMENTS 2073193A 3/1981 United Kingdom .

OTHER PUBLICATIONS

Ponec et al., Jour. of Cell. Phys. 133:358-364 (1987).
Chem. Abstract 97:4664v-236B, 12/24/81.
Chemical Engineering News, vol. 66, No. 31.
Abstracts of Papers American Chemical Society 196th ACS National Meeting (12/25/88-12/30/88 ISBN 8412-1493X).
Drugs of the Future, vol. 13, No. 5, 1988, p. 475.
Journal of Medicinal Chemistry, vol. 28, No. 4, Apr. 1985.
Clin. Pharm., 7/1, 21-36 (1988).
J. Cell Physiol., 133/2, 358-364 (1987).
Dialog Databank EMBASE Abstract of Document AR.
Dialog Databank EMBASE Abstract of Document AS.

*Primary Examiner*—Leonard Schenkman
*Attorney, Agent, or Firm*—George M. Gould; George W. Johnston; Alan P. Kass

[57] ABSTRACT

A method of treating hyperproliferative skin diseases, such as psoriasis, using a compound of formula

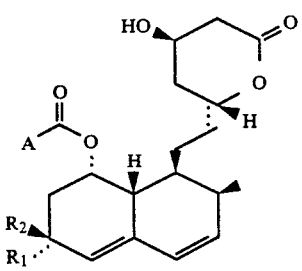

wherein
$R_1$ is hydrogen when $R_2$ is hydroxy, and $R_1$ is methyl when $R_2$ is hydrogen; and A is alkyl; cycloalkyl; alkenyl; alkyl substituted with trifluoromethyl; phenyl; halophenyl; phenyl-$C_{1-3}$ alkyl; phenyl-$C_{1-3}$ alkyl substituted on the phenyl with 1 to 3 substituents selected from the group consisting of halo, $C_{1-3}$ alkyl, and $C_{1-3}$ alkoxy; or
A is

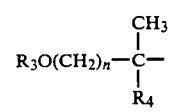

wherein $R_3$ is hydrogen or

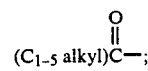

$R_4$ is hydrogen or methyl, and n is 1 to 5, or the corresponding hydroxy acid of formula

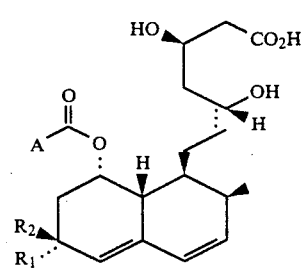

or a pharmaceutically acceptable salt of said acid, an alkyl ester of said acid, an acetylamino-substituted-$C_{1-4}$ alkyl ester of said acid, a phenyl-dimethylamino ester of said acid or a α-monoglyceride of said acid.

19 Claims, No Drawings

METHOD FOR INHIBITING HYPERPROLIFERATIVE DISEASES

BRIEF SUMMARY OF THE INVENTION

The invention relates to a method of treating hyperproliferative skin diseases, such as psoriasis, with compounds of the formula

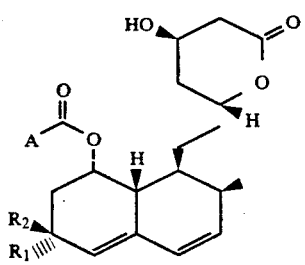

wherein
$R_1$ is hydrogen when $R_2$ is hydroxy and $R_1$ is methyl when $R_2$ is hydrogen; and A is alkyl; cycloalkyl; alkenyl; alkyl substituted with trifluoromethyl; phenyl; halophenyl; phenyl-$C_{1-3}$ alkyl; phenyl-$C_{1-3}$ alkyl substituted on the phenyl with 1 to 3 substituents selected from the group consisting of halo, $C_{1-3}$ alkyl, and $C_{1-3}$ alkoxy; or
A is

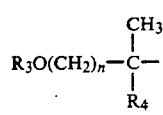

wherein
$R_3$ is hydrogen or

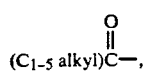

$R_4$ is hydrogen or methyl, and n is 1 to 5; or the corresponding hydroxy acid of formula

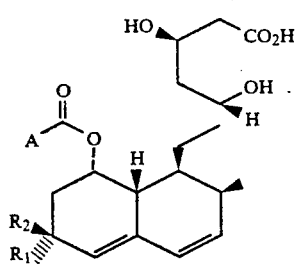

wherein A, $R_1$ and $R_2$ are as described above, or a pharmaceutically acceptable salt of said acid, an alkyl ester of said acid, an acetylamino-substituted-$C_{1-4}$ alkyl ester of said acid, a phenyl-dimethylamino ester of said acid or a α-monoglyceride of said acid.

BACKGROUND OF THE INVENTION

Compounds of formulas I-X and other mevinolin derivatives are known to inhibit the biosynthesis of cholesterol and thus are useful for their antihypercholesterolemic activity. (see U.S. Pat. No. 4,444,784 issued to Hoffman et al on Apr. 24, 1984 and U.S. Pat. No. 4,450,171 issued to Hoffman et al on May 22, 1984). The compounds of formula I-X may be isolated from the microfungus of the genus Aspergillus as described in U.S. Pat. Nos. 4,231,938 issued to Monaghan et al on Nov. 4, 1980 and U.S. Pat. No. 4,294,926 issued to Monaghan et al on Oct. 13, 1981.

The most active member of this group of natural compounds in inhibiting cholesterol biosynthesis has a mevinolin structure. (see U.S. Pat. No. 4,450,171, col. 1., lines 43-51; also see U.S. Pat. Nos. 4,444,784; 4,293,496; 4,450,171; 4,582,915; 4,231,938; 4,294,926; and 4,668,699 hereby incorporated by reference). As antihypercholesterolemic agents, these known compounds may be administered orally or parenterally, although the oral route is generally desirable. Moreover, the known compounds have been found to be useful as anti-fungal agents which may be sprayed or dusted on plants to be protected. (see U.S. Pat. No. 4,450,171, col. 12, lines 45-66).

DETAILED DESCRIPTION OF THE INVENTION

The invention relates to a method of treating hyperproliferative skin diseases, such as psoriasis, with compounds of the formula

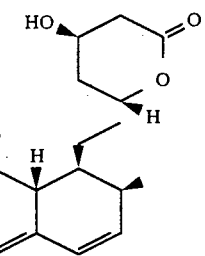

wherein $R_1$ is hydrogen when $R_2$ is hydroxy, and $R_1$ is methyl when $R_2$ is hydrogen; and A is alkyl; cycloalkyl; alkenyl; alkyl substituted with trifluoromethyl; phenyl; halophenyl; phenyl-$C_{1-3}$ alkyl; phenyl-$C_{1-3}$ alkyl substituted on the phenyl with 1 to 3 substituents selected from the group consisting of halo, $C_{1-3}$ alkyl, and $C_{1-3}$ alkoxy; or
A is

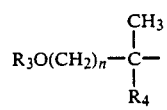

wherein $R_3$ is hydrogen or

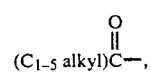

$R_4$ is hydrogen or methyl, and n is 1 to 5;

Preferred compounds of the formula I are compounds of formula

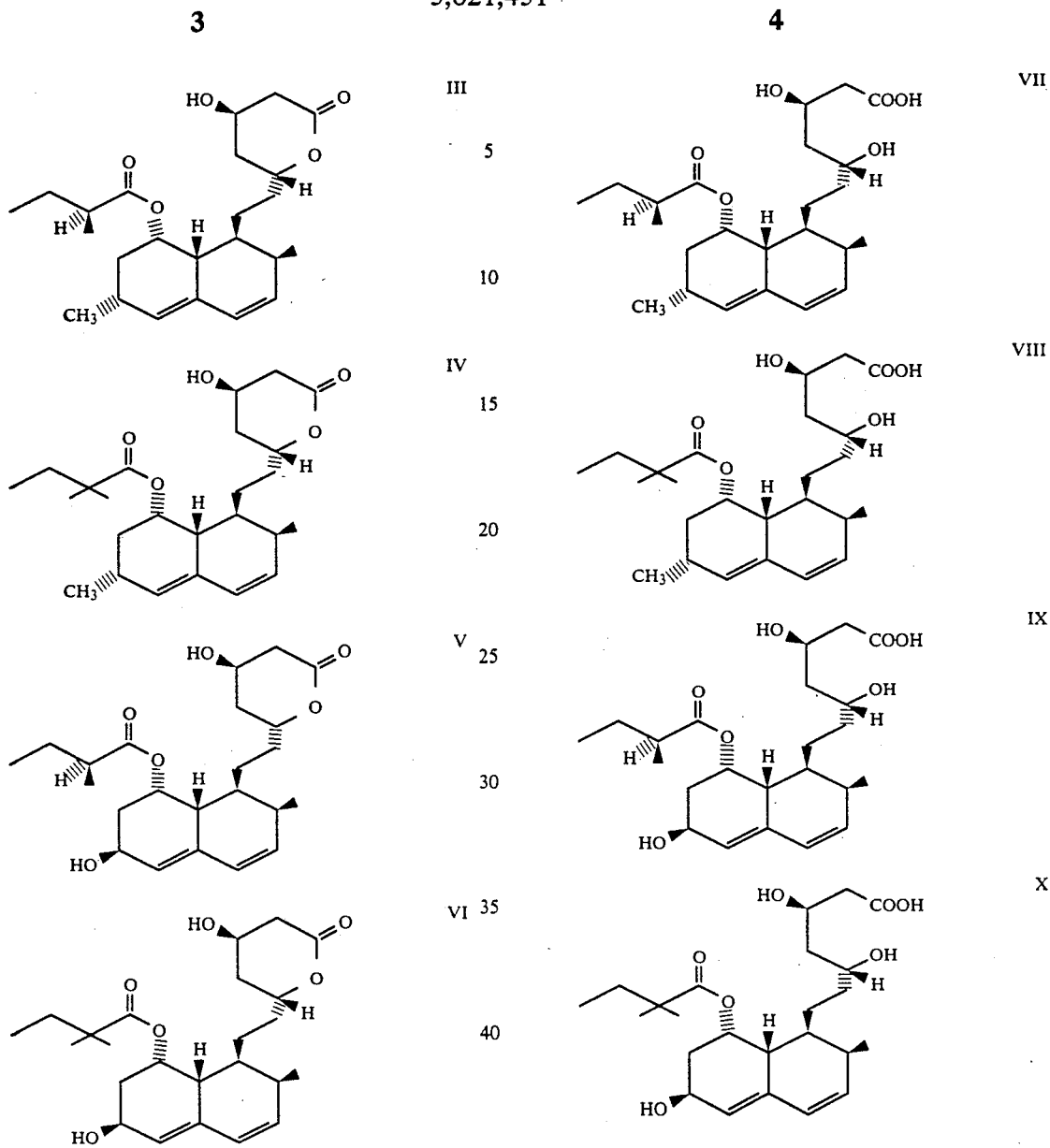

The corresponding hydroxy acid of formula I is

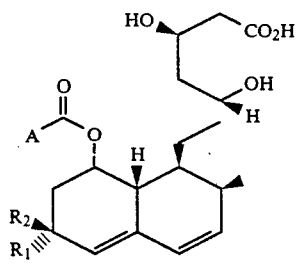

wherein A, $R_1$ and $R_2$ are as described above, or a pharmaceutically acceptable salt of said acid, an alkyl ester of said acid, an acetylamino-substituted-$C_{1-4}$ alkyl ester of said acid, a phenyl-dimethylamino ester of said acid or a α-monoglyceride of said acid.

Preferred compounds of formula II are compounds of formula

It has been unexpectedly found that compounds of formulas I-X are useful in the treatment of hyperproliferative skin diseases, such as psoriasis, basal cell carcinomas, squamous cell carcinomas, keratosis, and disorders of keratinization. These compounds may be administered either orally or topically.

Compounds of formulas I and II wherein $R_1$ is methyl and A is as described above may be prepared by methods disclosed in U.S. Pat. No. 4,444,784 and 4,450,171.

Compounds of formula I are converted into the compound of formula II in a manner analogous to that discussed in U.S. Pat. No. 4,444,784.

Compounds of formulas V, VI, IX and X may be prepared by known methods discussed in U.S. Pat. No. 4,346,227.

"Normal skin" is skin which undergoes a sequence of changes resulting from changes in the proliferative basal cells to the formation of terminally differentiated corneocytes. As the epidermis differentiates in the skin, keratinocytes undergo a destructive process of terminal differentiation to produce the acellular protective layer of the stratum corneum. The process begins with the basal layer of cells proliferating and entering into the spinous layer of the skin. Within the spinous layer there is increased metabolic activity with a concomitant increase in the precursor protein for the cornified envelope and changes in the keratin expression. As the cells pass higher up the skin into the stratum corneum, enzymes responsible for crosslinking envelope proteins are active, profilaggrin processing is initiated, and higher molecular weight keratins appear. As the cell passes into the stratum corneum it is converted into a keratin filled, cornified envelope without nucleus or other organelles.

As used herein, the term "psoriasis" refers to a hyperproliferative skin disease which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The terms "keratosis," "basal cell carcinomas" and "disorders of keratinization" refer to hyperproliferative skin diseases in which the regulatory mechanisms for the proliferation and differentiation of normal skin cells are disrupted.

The compounds of formulas I-X are active as skin hyperproliferation antagonists, that is, as agents which decrease the proliferation of human keratinocytes. The compounds further antagonize alterations in the differentiation of keratinocytes. Accordingly, the compounds are useful as agents for the treatment of hyperproliferative skin diseases such as psoriasis, basal cell carcinomas, disorders of keratinization and keratosis.

As used herein the term "halo" means chloro, fluoro, bromo, or iodo.

As used herein the term "alkyl" denotes a straight or branched chain saturated hydrocarbon having 1 to 10 carbon atoms such as methyl, ethyl, propyl, isopropyl and the like.

The term "cycloalkyl" denotes a cycloalkyl having 3 to 10 carbon atoms such as cyclopropyl, cyclobutyl, and the like.

The term "alkenyl" denotes a straight or branched chain alkenyl having 2 to 10 carbon atoms such as ethenyl, propenyl and the like.

The term "alkyl substituted with trifluoromethyl" denotes a $C_{1-10}$ straight or branched chain alkyl having one hydrogen replaced by trifluoromethyl.

The term "halophenyl" denotes a phenyl substituted with up to three halogens.

The term "phenyl-$C_{1-3}$ alkyl" denotes an alkyl having 1-3 carbon atoms and one of whose hydrogens is replaced by a phenyl.

The term "corresponding hydroxy acid of formula I" denotes a compound of the formula

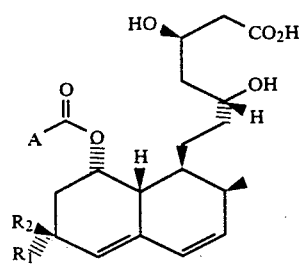

wherein A, $R_1$ and $R_2$ are as described above.

In the formulas presented herein, the various substituents are illustrated as joined to the carbon framework by one of the following notations: a solid line () indicates a substituent which is above the plane of the molecule ($\beta$-orientation) and a dotted line () or () indicates a substituent which is below the plane of the molecule ($\alpha$-orientation).

The invention relates to a method for treating hyperproliferative skin diseases which comprises administering an antihyperproliferatively effective amount of a compound of formula

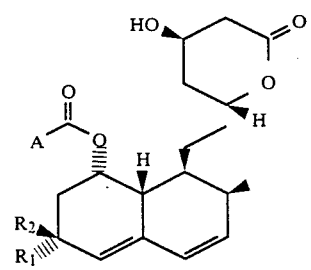

wherein $R_1$, $R_2$ and A are as described above, or the corresponding hydroxy acid of the formula

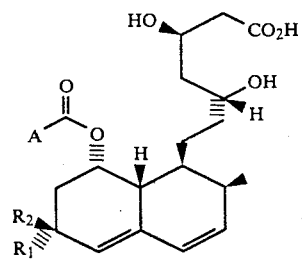

wherein $R_1$, $R_2$ and A are as described above or a pharmaceutically acceptable salt of said acid, an alkyl ester of said acid, an acetylamino-substituted-$C_{1-4}$ alkyl ester of said acid, a phenyl-dimethylamino ester of said acid or a $\alpha$-monoglyceride of said acid.

The invention also relates to oral and topical compositions comprising an effective amount of a compound of formulas I-X.

Preferred are compounds of formulas I and II wherein $R_1$ is hydrogen when $R_2$ is hydroxy or $R_1$ is methyl when $R_2$ is hydrogen.

Especially preferred of the compounds of formula I is the compound of the formula

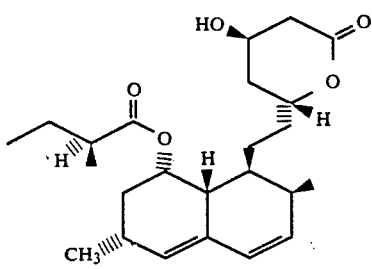

which is referred to herein as mevinolin; and also especially preferred of the compounds of formula I is the compound of the formula

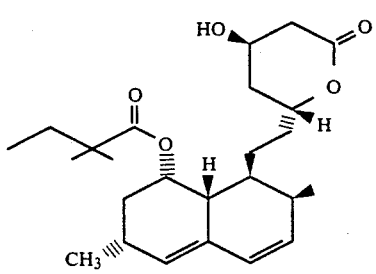

which is referred to herein as synvinolin.

The compounds of formulas III and IV are known or can be prepared in accordance with known methods, such as those described in U.S. Pat. No. 4,346,227.

Effect of Compounds of Formulas I–X on the Proliferation of Cultured Human Keratinocytes The compounds of formulas I–X as described above can be administered orally, for the treatment of hyperproliferative skin diseases such as psoriasis, basal cell carcinomas, squamous cell carcinomas, disorders of keratinization and keratosis to warm-blooded animals which need such treatment. While dosages may vary depending upon the severity of the disease, the compounds of formulas I–X can be administered orally to the adult human in dosages that are in the range of about 10 to 80 milligrams per day and preferably about 10–50 milligrams per day for the treatment of hyperproliferative skin diseases such as psoriasis, basal cell carcinomas, squamous cell carcinomas, disorders of keratinization and keratosis.

The compounds of formulas I–X as described above can be administered topically, for treatment of hyperproliferative skin diseases, such as psoriasis, basal cell carcinomas, squamous cell carcinomas, disorders of keratinization and keratosis to warm-blooded animals which need such treatment. While dosages may vary depending upon the severity of the disease, the compounds of formulas I–X as described above can be administered topically in dosages that are about 1 to about 200 micrograms of compounds I–X per gram of topical formulation per day for the treatment of such diseases, preferably about 1 to about 50 micrograms of the compounds of formulas I–X per gram of topical formulation per day are administered to a patient.

The useful activity of compounds of formulas I–X as agents for the treatment of hyperproliferative skin diseases are demonstrated by the following test procedures.

Materials & Methods

1. Culture Conditions

Human neonatal foreskins were collected by circumcision and placed into tubes containing DMEM media. Upon arrival at the laboratory the foreskins were mechanically trimmed of excess dermis and treated with a solution of trypsin/EDTA (0.05%/0.02%) at 4° C. overnight. The epidermis was stripped from the dermis, agitated in buffered saline to remove basal keratinocytes and to separate the stratum corneum which was subsequently removed. The separated cells were centrifuged, resuspended in media, counted and the keratinocytes were plated onto a plain plastic culture dish.

The keratinocytes were plated at a density of about $10^5$ cells/cm$^2$ in 35 cm$^2$ dishes. The cells were grown in keratinocyte growth media (KGM ®-modified MCDB 153 containing antibiotics by Clonetics of Boulder, Colo.) according to protocols originally developed by Boyce, S.T. and Ham, R.G., *J. of Tissue Culture Meth.* 9:83-93 (1985). The cells were grown for 5–10 days and changed every 2–3 days with keratinocyte growth media with 1.5 mM CaCl$_2$ (hereinafter KGM ®/1.5 mM CaCl$_2$) until cells reached a 75% confluency by visual observation. All the cultures were incubated in a humidified atmosphere of 5% CO$_2$ at 37° C.

To establish keratinocyte cell cultures as antiproliferative assays, cells prepared as described in the foregoing were washed with PBS and removed from the culture surface with a solution of trypsin/EDTA (0.25%/.0.03%). The removed cells were then centrifuged, resuspended in the KGM ®/1.5 CaCl$_2$ and counted. The cells were then distributed to 6 well plates at 100,000 cells per well as described in the foregoing. Each well had an area of 9.5 cm$^2$. After 24–48 hours fresh KGM ®/1.5 mM CaCl$_2$ which contained test compounds was added to the cells. The cultures were maintained for seven days. The media and test compound was changed every 2–3 days.

Solutions of the test compounds were prepared as follows: 1 milligram quantities were received in amber glass vials, and stored at −20° C. Sufficient 100% ethanol was added directly to vials to obtain a millimolar solution that was subsequently aliquoted into small amber vials, overlayed with argon gas and stored at −20° C. Each stock solution was thawed once, used and discarded. Aliquots from the stock solutions were diluted directly into medium and then serially diluted from micromolar to $10^{-12}$M concentrations. Dilutions from $10^{-7}$M to $10^{-12}$M had ethanol added for a final concentration of 0.1%. Stock solutions were used within one month. Control cultures were treated with 0.1% ethanol.

3. Cell Proliferation

For each experiment every culture well received the same number of cells from the same culture source. At the termination of the experiment the number of cells per was determined by the following procedure. Wells were washed twice with PBS and then incubated for approximately 10–20 minutes at 37° C. with a trypsin/EDTA solution (0.25%/03%). PBS plus 0.1% soybean trypsin inhibitor was added and the cells were suspended. An aliquot of the cells was placed into isotonic buffered saline and counted on an electronic particle counter (e.g. Coulter Counter ® device by Coulter Electronics of Hialeah, Fla.).

Quantification of proliferation was done by enumerating the number of keratinocyte cells in each well using the Coulter Counter ®. Results shown in Table 1 below show the percent reduction or inhibition of keratinocyte cells calculated for each of 4 concentrations of the compounds tested according to the formula:

$$\left[1 - \left(\frac{\text{mean number of cells in experimental cultures}}{\text{mean number of cells in control cultures}}\right)\right] \times 100$$

For statistical analysis, the mean was calculated for all wells in each treatment group. Standard deviation was determined by nonbiased analysis using a value for the number of wells in each group, which was 3.

TABLE 1
INHIBITION OF COMPOUNDS OF FORMULA I on KERATINOCYTE PROLIFERATION

| Compound | Dosage of Compound (M) | Percent Inhibition on Keratinocyte Proliferation | Standard Deviation |
|---|---|---|---|
| 1. ETOH Control | | 0.00 | 24.48 |
| 2. Mevinolin | $10^{-10}$ | 23.2 | 26.7 |
| | $10^{-8}$ | 28.9 | 17.57 |
| | $10^{-7}$ | 38.6 | 12.82 |
| | $10^{-6}$ | 84.21 | 14.51 |
| 3. Synvinolin | $10^{-10}$ | 0.00 | 24.08 |
| | $10^{-8}$ | 11.17 | 26.42 |
| | $10^{-7}$ | 33.60 | 26.34 |
| | $10^{-6}$ | 62.06 | 24.31 |

Each compound is tested in triplicate, at each concentration.

Conclusion

The foregoing results evidence that compounds of formula I at a dosage of $10^{-6}$M inhibit keratinocyte cell proliferation at a rate greater than 50% without toxicity to the cells. For example, mevinolin at this dosage inhibits 84.21% of keratinocyte proliferization and synvinolin inhibits 62.06% of keratinocyte proliferization at this dosage.

These data indicate that the compounds of formula I restrain the proliferation of human keratinocyte cells in vitro, without toxicity to the cells. From these results it can be seen that each of the tested compounds is useful as an agent in the treatment of hyperproliferative skin diseases such as psoriasis.

As pointed out above, it is known that compounds of formula I are useful as cholesterol lowering agents. It is also known that corresponding hydroxyacids of formula II are useful as cholesterol lowering agents.

In the present invention it has been found that compounds which have cholesterol lowering activity are also useful in the treatment of hyperproliferative skin diseases.

Dosage Forms

Oral dosage forms comprising compounds of formulas I-X of the invention may be incorporated in capsules, tablets and the like with pharmaceutically acceptable carrier materials.

Illustrative of the pharmaceutically acceptable carrier materials which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

A preferable formulation for an oral dosage of the compound of Formulas I-X in capsule form is presented in Example 1 below:

Example 1

Oral dosage formulation (capsule) for Compounds of Formulas I-X.

| | | |
|---|---|---|
| 1. | Compound of Formula I, II, III, IV, V, VI, VII, VIII, IX or X | 20 milligrams |
| 2. | Lactose hydrose | 150 milligrams |
| 3. | Starch | 30 milligrams |
| 4. | Talc | 20 milligrams |

Manufacturing Process

A. Mix 1 with a portion of 2.
B. Add 3 and 4, and mix.
C. Add the remainder of 2, mix thoroughly, and pass through a suitable mill. Capsules are filled with the composition thus prepared.

Topical dosage forms comprising compounds of formulas I-X of the invention include: ointments and creams encompassing formulations having oleaginous, adsorbable, water-soluble and emulsion-type bases such as petroleum, lanolin, polyethylene glycols and the like.

Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like.

Gels are semi-solid preparations made by gelling a solution or suspension of the active ingredient in a carrier vehicle. The vehicles, which can be hydrous or anhydrous, are gelled using a gelling agent, such as carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of inflammation for the exertion of local action. Accordingly, the topical compositions include those pharmaceutical forms in which the compound is applied externally by direct contract with the skin. The topical dosage forms comprise gels, creams, lotions, ointments, powders, aerosols and other conventional forms for applying medications to the skin obtained by admixing the compounds of formula I with known pharmaceutical topical carrier materials. In addition to the application to the skin, the topical compositions of this invention can also be employed in the treatment of inflammations of mucous membranes, where such membranes are accessible to topical application of medication. For example, the topical composition can be applied to the mucous lining of the mouth or lower colon.

A preferable formulation for a topical dosage of the compounds of Formulas I-X is presented in Example 2 below:

Example 2

Preferred Formulation for Topical Dosage of Compounds of Formulas I-X

| | | |
|---|---|---|
| 1. | Compound of Formula I, II, III, IV, V, VI, VII, VII, IX or X | 10.0 micrograms |
| 2. | Stearyl alcohol | 4.0 g |
| 3. | Cetyl alcohol | 4.0 g |
| 4. | Mineral oil | 3.0 g |
| 5. | Polysorbate 60 | 4.5 g |
| 6. | Sorbitan stearate | 4.5 g |
| 7. | Propylene glycol | 10.0 g |
| 8. | Methyl paraben | 0.18 g |
| 9. | Propyl paraben | 0.02 g |
| 10. | Water | q.s. to 100.00 g |

Manufacturing Process

A. Heat 2 through 6 to 80° C., which melts all ingredients (oil phase).
B. Dissolve 1 in oil phase.
C. Heat 7 and 10 to 90° C (aqueous phase).
D. Dissolve 8 and 9 in aqueous phase.
E. Add aqueous phase to the oil phase and stir rapidly to form emulsion.
F. Cool slowly to 50° C. to allow to congeal.
G. Continue stirring slowly to room temperature.

We claim:

1. A method for treating a hyperproliferative skin disease in a patient in need of treatment of such skin disease comprising: administering an antihyperproliferatively effective amount of a compound of formula

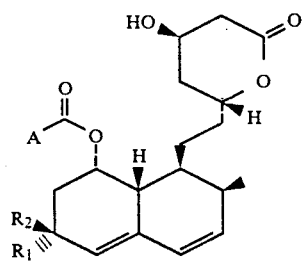

I wherein $R_1$ is hydrogen or methyl and $R_2$ is hydroxy or hydrogen, with the proviso that when $R_1$ is hydrogen, $R_2$ is hydroxy and when $R_1$ is methyl, $R_2$ is hydrogen; and A is alkyl; cycloalkyl; alkenyl; alkyl substituted with trifluoromethyl; phenyl; halophenyl; phenyl-$C_{1-3}$ alkyl; phenyl-$C_{1-3}$ alkyl substituted on the phenyl with 1 to 3 substituents selected from the group consisting of halo, $C_{1-3}$ alkyl, or $C_{1-3}$ alkoxy; or A is

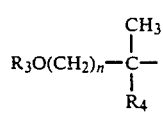

wherein $R_3$ is hydrogen or

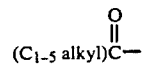

$R_4$ is hydrogen or methyl, and n is 1 to 5.

2. The method of claim 1 wherein A is alkyl.

3. The method of claim 2 wherein the compound is a compound of formula

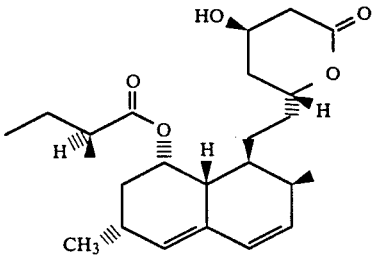

III

4. The method of claim 2 wherein the compound is a compound of formula

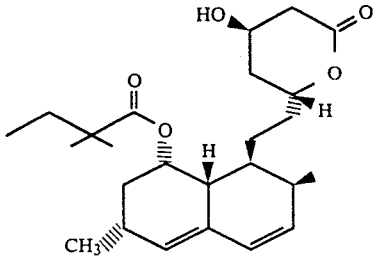

IV

5. The method of claim 2 wherein the compound is a compound of formula

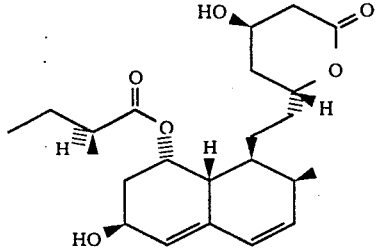

V

6. The method of claim 2 wherein the compound is a compound of formula

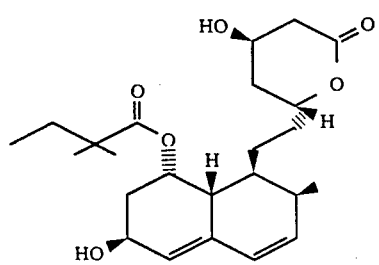

VI

7. The method of claim 1 wherein the compound of formula I is orally administered.

8. The method of claim 7 wherein the dosage range of the compound of formula I is about 10 to about 80 milligrams per day.

9. The method of claim 1 wherein the compound of formula I is administered topically.

10. The method of claim 9 wherein said dosage range of the compound of formula I is about 1 to about 200 micrograms per gram of a composition.

11. A method for treating a hyperproliferative skin disease in a patient in need of treatment of such skin disease comprising administering antihyperproliferatively effective amount of a compound of formula

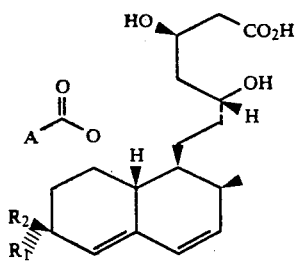

II wherein $R_1$ is hydrogen or methyl and $R_2$ is hydroxy or hydrogen, with the proviso that when $R_1$ is hydrogen, $R_2$ is hydroxy and when $R_1$ is methyl, $R_2$ is hydrogen; and A is alkyl; cycloalkyl; alkenyl; alkyl substituted with trifluoromethyl; phenyl; halophenyl; phenyl-$C_{1-3}$ alkyl; phenyl-$C_{1-3}$ alkyl substituted on the phenyl with 1 to 3 substituents selected from the group consisting of halo, $C_{1-3}$ alkyl, or $C_{1-3}$ alkoxy; or A is

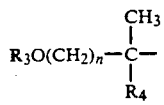

wherein $R_3$ is hydrogen or

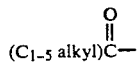

$R_4$ is hydrogen or methyl, and n is 1 to 5, or a pharmaceutically acceptable salt of said acid, an alkyl ester of said acid, an acetylamino-substituted-$C_{1-4}$ alkyl ester of said acid, a phenyl-dimethylamino ester of said acid or a α-monoglyceride of said acid.

12. A pharmaceutical composition for topical administration to a patient in need of treatment of hyperproliferative skin disease comprising: a pharmaceutical carrier in the form of an ointment, cream, lotion or gel, powder and an antihyperproliferatively effective amount of a compound of formula

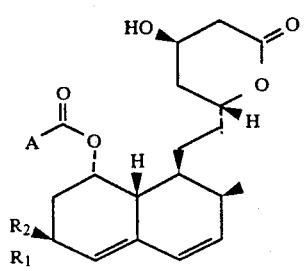

I wherein $R_1$ is hydrogen or methyl and $R_2$ is hydroxy or hydrogen, with the proviso that when $R_1$ is hydrogen, $R_2$ is hydroxy and when $R_1$ is methyl, $R_2$ is hydrogen; and A is alkyl; cycloalkyl; alkenyl; alkyl substituted with trifluoromethyl; phenyl; halophenyl; phenyl-$C_{1-3}$ alkyl; phenyl-$C_{1-3}$ alkyl substituted on the phenyl with 1 to 3 substituents selected from the group consisting of halo, $C_{1-3}$ alkyl, or $C_{1-3}$ alkoxy, or A is

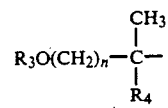

wherein $R_3$ is hydrogen or

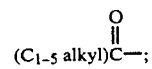

$R_4$ is hydrogen or methyl, and n is 1 to 5.

13. A composition in accordance with claim 12 wherein A is alkyl.

14. A composition in accordance with claim 13 wherein the compound is of the formula

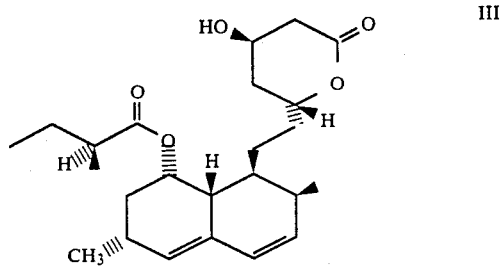

III

15. A composition in accordance with claim 13 wherein the compound is a compound of the formula

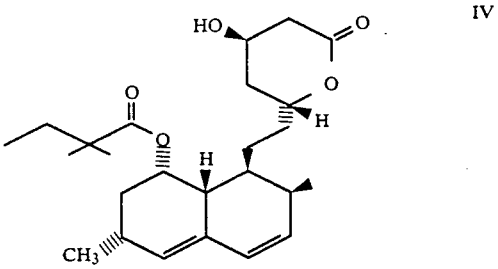

IV

16. A composition in accordance with claim 13 wherein the compound is a compound of formula

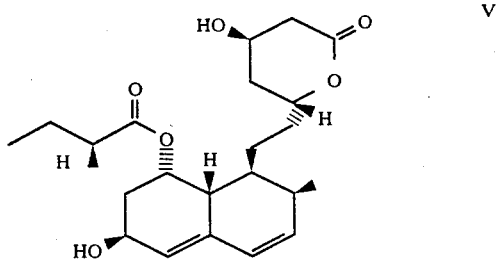

V

17. A composition in accordance with claim 13 wherein the compound is a compound of formula

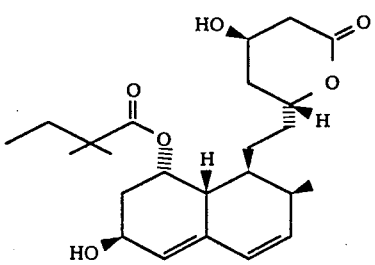

18. A composition in accordance with claim 12, comprising about 1 to about 200 micrograms of a compound of formula I per gram of composition.

19. A pharmaceutical composition for topical administration to a patient in need of treatment of hyperproliferative skin disease comprising: a pharmaceutical carrier in the form of an ointment, cream, lotion or gel, and an antihyperproliferatively effective amount of a compound of formula

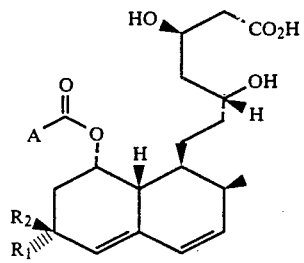

wherein $R_1$ is hydrogen or methyl and $R_2$ is hydroxy or hydrogen, with the proviso that when $R_1$ is hydrogen, $R_2$ is hydroxy and when $R_1$ is methyl, $R_2$ is hydrogen; and A is alkyl; cycloalkyl; alkenyl; alkyl substituted with trifluoromethyl; phenyl; halophenyl; phenyl-$C_{1-3}$ alkyl; phenyl-$C_{1-3}$ alkyl substituted on the phenyl with 1 to 3 substituents selected from the group consisting of halo, $C_{1-3}$ alkyl, or $C_{1-3}$ alkoxy; or A is

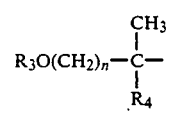

wherein $R_3$ is hydrogen or

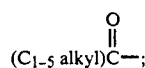

$R_4$ is hydrogen or methyl, and n is 1 to 5, or a pharmaceutically acceptable salt of said acid, an alkyl ester of said acid, an acetylamino-substituted-$C_{1-4}$ alkyl ester of said acid, a phenyl-dimethylamino ester of said acid or a α-monoglyceride of said acid.

* * * * *

UNITED STATES PATENT AND TRADEMARK OFFICE
CERTIFICATE OF CORRECTION

PATENT NO. : 5,021,451     Page 1 of 3

DATED : June 4, 1991

INVENTOR(S) : McLane et al.

It is certified that error appears in the above-identified patent and that said Letters Patent is hereby corrected as shown below:

Claim 11, column 13, line 8, between "administering" and "antihyperprolifera-" insert -- an --;

Claim 11, column 13, lines 10-20, delete the chemical formula as shown and insert therefor

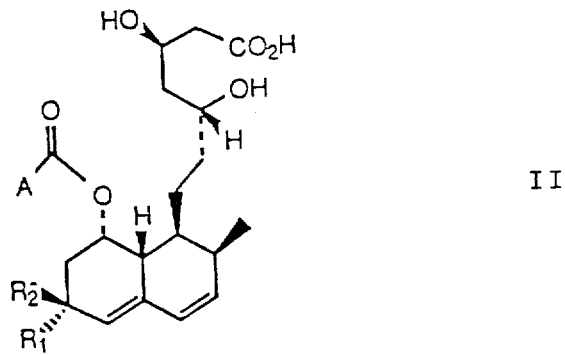

II

Claim 12, column 13, line 51, delete "powder";

Claim 12, column 13, lines 55 through 64, delete the chemical formula as shown and insert therefor

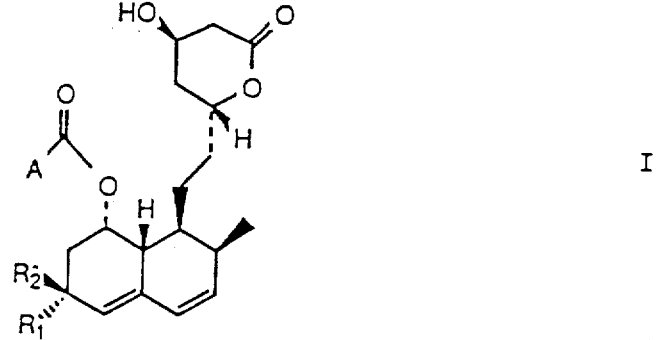

I

UNITED STATES PATENT AND TRADEMARK OFFICE
CERTIFICATE OF CORRECTION

PATENT NO. : 5,021,451

DATED : June 4, 1991

INVENTOR(S) : McLane et al.

It is certified that error appears in the above-identified patent and that said Letters Patent is hereby corrected as shown below:

Claim 12, column 14, line 5, delete "$C_{1-3}$ alkoxy, or A is" and insert therefor -- $C_{1-3}$-alkoxy; or A is --;

Claim 16, column 14, lines 55 through 66, delete the chemical formula as shown and insert therefor

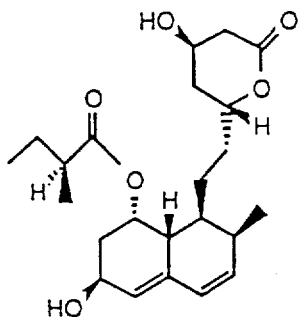

V

Claim 19, column 16, line 18, delete "phenyl-$C_{1-3}$ alkyl; phenyl-C1-3" and insert therefor -- phenyl-$C_{1-3}$ alkyl; phenyl-$C_{1-3}$--;

UNITED STATES PATENT AND TRADEMARK OFFICE
CERTIFICATE OF CORRECTION

PATENT NO. : 5,021,451   Page 3 of 3

DATED : June 4, 1991

INVENTOR(S) : Mclane etal.

It is certified that error appears in the above-identified patent and that said Letters Patent is hereby corrected as shown below:

Claim 19, column 16, line 37, delete "e" and insert therefor --ester of --;

Signed and Sealed this

Eighth Day of December, 1992

*Attest:*

DOUGLAS B. COMER

*Attesting Officer*   Acting Commissioner of Patents and Trademarks